United States Patent
Shigemori

(10) Patent No.: US 8,225,209 B2
(45) Date of Patent: Jul. 17, 2012

(54) CAPSULE ENDOSCOPE IMAGE DISPLAY DEVICE

(75) Inventor: Toshiaki Shigemori, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 419 days.

(21) Appl. No.: 12/626,748

(22) Filed: Nov. 27, 2009

(65) Prior Publication Data

US 2010/0115469 A1    May 6, 2010

Related U.S. Application Data

(63) Continuation of application No. PCT/JP2008/001163, filed on May 8, 2008.

(30) Foreign Application Priority Data

May 29, 2007 (JP) ................................ 2007-141462

(51) Int. Cl.
*G06F 3/00* (2006.01)
(52) U.S. Cl. ...................................................... 715/730
(58) Field of Classification Search .................. 715/730, 715/732, 838
See application file for complete search history.

(56) References Cited

U.S. PATENT DOCUMENTS

| | | | |
|---|---|---|---|
| 6,346,940 B1 * | 2/2002 | Fukunaga | 345/427 |
| 6,578,488 B2 | 6/2003 | Strauss et al. | |
| 7,978,890 B2 * | 7/2011 | Yamagishi et al. | 382/128 |
| 2002/0177779 A1 | 11/2002 | Adler et al. | |
| 2006/0202998 A1 | 9/2006 | Hirakawa et al. | |
| 2007/0066875 A1 | 3/2007 | Horn et al. | |
| 2007/0255095 A1 * | 11/2007 | Gilreath et al. | 600/102 |

FOREIGN PATENT DOCUMENTS

| | | |
|---|---|---|
| EP | 1 170 570 A2 | 1/2002 |
| JP | 2002-224045 | 8/2002 |
| JP | 2005-218584 | 8/2005 |
| JP | 2007-61638 | 3/2007 |
| JP | 2007-75156 | 3/2007 |
| JP | 2007-105458 | 4/2007 |
| WO | WO 2007/029813 A1 | 3/2007 |

OTHER PUBLICATIONS

International Search Report dated Jun. 3, 2008.

* cited by examiner

*Primary Examiner* — Thanh Vu
(74) *Attorney, Agent, or Firm* — Scully, Scott, Murphy Presser, P.C.

(57) ABSTRACT

A capsule endoscope image display device displays, on a display screen, at least a search character input window, a thumbnail specification input button for specifying a thumbnail, and a report specification input button for specifying a report. When the thumbnail specification input button is operated, thumbnails to which a comment including characters input in the search character input window is added are searched for in a recording device, and their listing is displayed in a scrollable manner. When the report specification input button is operated, reports including the characters input in the search character input window are searched for, and their listing is displayed in a scrollable manner. In this way, data associated with an image of desired position, lesion portion, etc. can be easily grasped from among many pieces of image information.

21 Claims, 9 Drawing Sheets

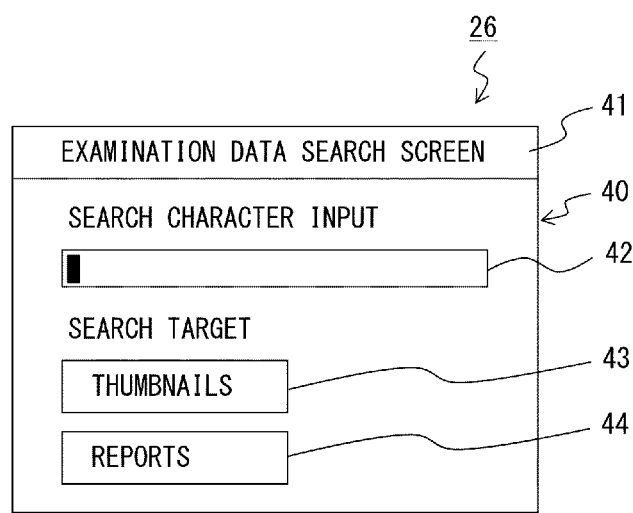
F I G. 4

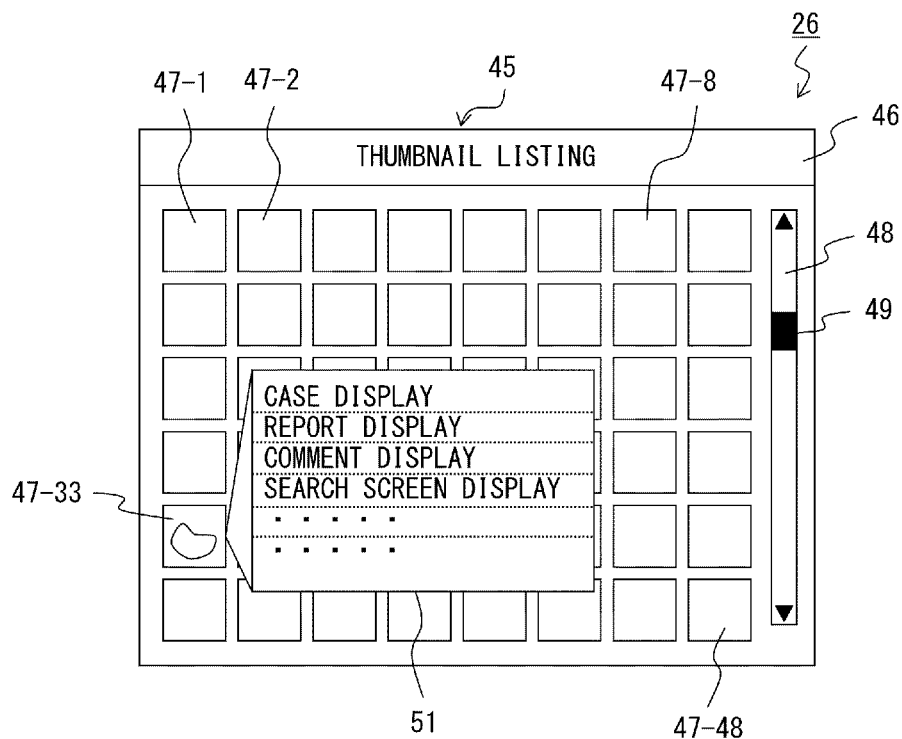
F I G. 5

CAPSULE ENDOSCOPE IMAGE DISPLAY DEVICE

CROSS REFERENCE TO RELATED APPLICATIONS

This is a Continuation Application of PCT Application No. PCT/JP2008/001163, filed May 8, 2008, which was not published under PCT Article 21 (2) in English.

This application is based upon and claims the benefit of priority from the prior Japanese Patent Application No. 2007-141462, filed in May 29, 2007 the entire contents of which are incorporated herein by reference.

BACKGROUND OF THE INVENTION

1. Field of the Invention

The present invention relates to a capsule endoscope image display device for executing a display process of information about a plurality of pieces of images obtained by being captured over an elapse of time while a capsule endoscope autonomously or heteronomously moves within a body to be examined, and of information associated with the image information.

2. Description of the Related Art

In recent years, a so-called capsule endoscope, which is a swallow-type endoscope, has made its debut in the endoscope field. US Patent Publication No. 2002/0177779A1 discloses the technique for providing a capsule endoscope with an image capturing function and a wireless communication function, for sequentially capturing images of organs such as the stomach, the small intestine, etc., during an observation period from when the capsule endoscope is swallowed via the mouth of a patient for an observation or an examination until when it is naturally excreted from the body, and for sequentially and wirelessly transmitting image information (electronic data that represents images) obtained by capturing the images.

Additionally, Japanese Laid-open Patent Publication No. 2005-218584 (Abstract, FIGS. 1, 2, and 3) discloses the technique by which image information wirelessly transmitted as described above is received by a receiver provided outside the body of a patient and stored in a predetermined memory, and a doctor can thereafter use the image information for a diagnosis, etc. by reading the image information and displaying the image information on a display screen, depending on need.

However, for such a capsule endoscope, the period from when it is swallowed via the mouth of a patient until when it is naturally excreted is an observation period or an examination period that is unlike that in a normal endoscope.

Case data shot with the capsule endoscope during this period is composed of approximately 60,000 images as materials shot for the maximum of approximately eight hours, and the number of pieces of image information (case data) is extremely large.

In addition, information about images shot with the capsule endoscope in the past include image information of many patients, and also information about images shot on different examination dates even for the same patient, and are stored in a recording device.

It is not easy for a doctor to grasp such an extremely large number of pieces of image information in a short time at the time of a diagnosis, etc., and to search for image information of a desired portion to be focused on, or more specifically, only image information of an organ desired to be diagnosed, or only image information obtained by shooting a lesional portion, etc.

Additionally, it is not easy to search for only an image itself, or only data included in such image information and associated with a desired case such as a comment, a report, etc. on results of a diagnosis made by a previously responsible doctor.

Patent Document 1: US Patent Publication No. 2002/0177779A1

Patent Document 2: Japanese Laid-open Patent Publication No. 2005-218584

SUMMARY OF THE INVENTION

An object of the present invention is to provide a capsule endoscope image display device that can easily grasp data associated with an image obtained by shooting a desired position, lesional portion, etc. to be focused on from among many pieces of image information.

To achieve the above described object, the capsule endoscope image display device according to the present invention is a capsule endoscope image display device for storing, in a recording device (i.e. a storage device), image information of a plurality of images obtained by being captured in a plurality of positions within a body to be examined over an elapse of time by an image capturing device introduced into the body to be examined, for reading the image information from the recording device, and for displaying the read image information on a display screen, and includes: image displaying means for displaying a capsule endoscope image; thumbnail generating means for generating a thumbnail of an image to be focused on from the capsule endoscope image; thumbnail storing means for recording the generated thumbnail in the recording device; report creating means for creating a report of a capsule endoscope examination; report storing means for storing the created report in the recording device; search screen displaying means for displaying a search character input window on the display screen; search character inputting means for inputting a character in the search character input window; thumbnail searching means for searching for a thumbnail to which a comment including the same character as the character input in the search character input window is added, or which includes supplementary information including the same character; thumbnail listing displaying means for displaying a listing of thumbnails searched for by the thumbnail searching means on the display screen; report searching means for searching for a report including the same character as the character input in the search character input window, or which includes supplementary information including the same character; and report listing displaying means for displaying a listing of reports searched for by the report searching means on the display screen.

A capsule endoscope image display program according to the present invention is a capsule endoscope image display program for storing, in a recording device, image information of a plurality of images obtained by being captured in a plurality of positions within a body to be examined over an elapse of time by an image capturing device introduced into the body to be examined, for reading the image information from the recording device, and for displaying the read image information on a display screen, and includes: an image displaying step of displaying a capsule endoscope image; a thumbnail generating step of generating a thumbnail of an image to be focused on from the capsule endoscope image; a thumbnail storing step of recording the generated thumbnail in the recording device; a report creating step of creating a report of a capsule endoscope examination; a report storing step of storing the created report in the recording device; a search screen displaying step of displaying a search character input window on the display screen; a search character inputting step of inputting a character in the search character input window; a thumbnail searching step of searching for a thumbnail to which a comment including the same character as the character input in the search character input window is added, or which includes supplementary information including the same character; a thumbnail listing display step of displaying a listing of thumbnails searched for by the thumbnail searching step on the display screen; a report searching step of searching for a report including the same character as the character input in the search character input window, or which includes supplementary information including the same character; and a report listing displaying step of displaying a listing of reports searched for by the report searching step on the display screen.

According to the present invention, at least a search character input window, a thumbnail specification input button, and a report specification input button are displayed on a display screen, and a listing of thumbnails or reports is displayed on the display screen in response to an input operation performed for the input window or the button, whereby a doctor or a nurse can quickly grasp and verify case data having his or her desired characteristic.

BRIEF DESCRIPTION OF THE DRAWINGS

FIG. 4 illustrates an example of an examination data search screen displayed on the display screen of the monitor device in a capsule endoscope image display device (workstation) as a first embodiment;

FIG. 5 illustrates an example of a thumbnail listing screen displayed on the display screen of the monitor device in the capsule endoscope image display device (workstation) as the first embodiment;

Figure 1:
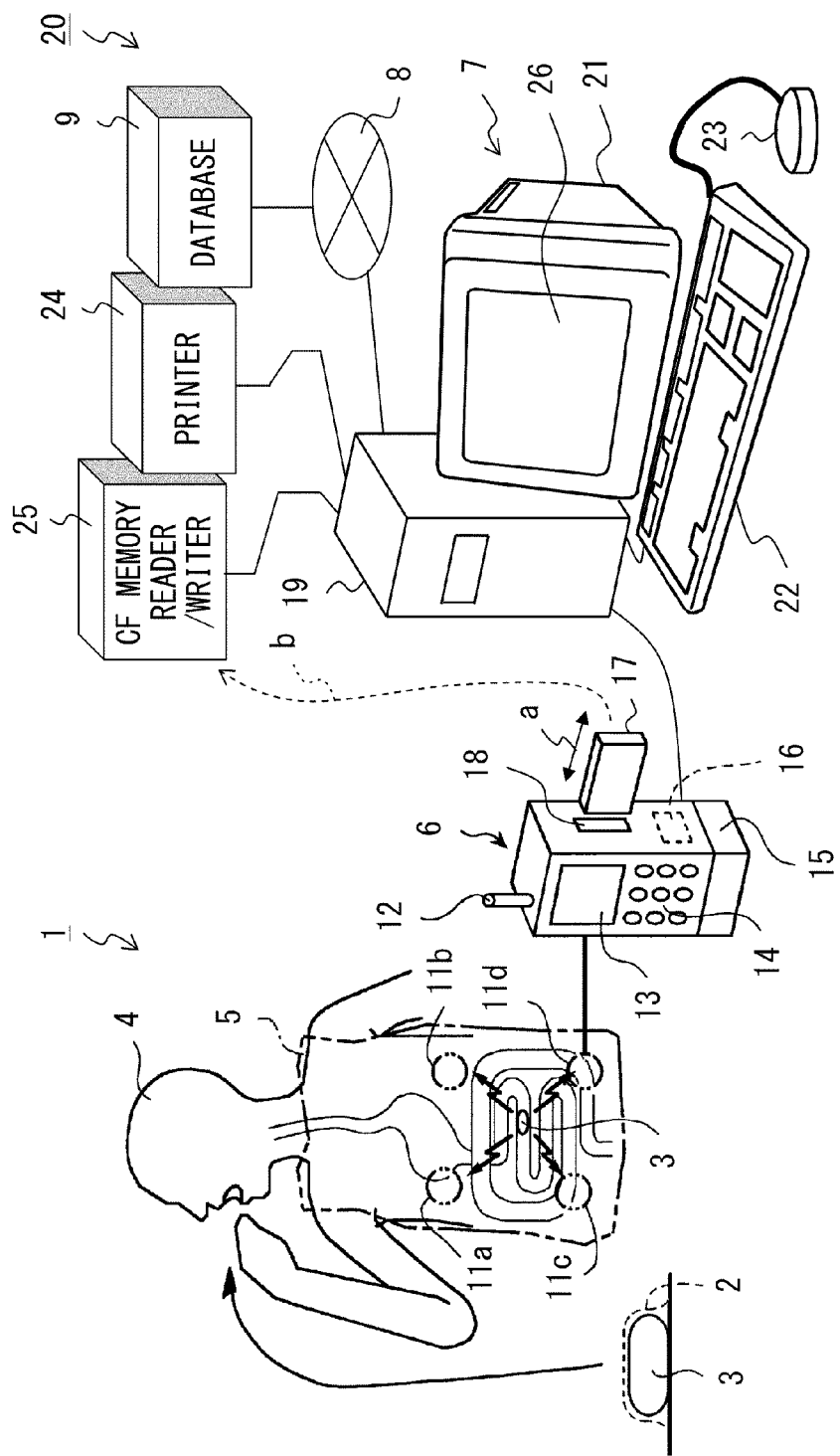
FIG. 1 schematically illustrates a basic configuration of a capsule endoscope system according to the present invention, and a capsule endoscope image filing system included therein.

EXPLANATION OF CODES 1 capsule endoscope system
2 package
3 capsule endoscope
4 person to be examined
5 jacket
6 receiver
7 workstation
8 network
9 recording device
11 (11a, 11b, 11c, 11d) antennas
12 antenna
13 display unit
14 input unit
15 power supply unit
16 signal processing/controlling unit
17 CF (Compact Flash (registered trademark)) memory
18 slot
19 main body device
20 capsule endoscope image filing system
21 monitor device
22 keyboard
23 mouse
24 printer
25 CF memory reader/writer
26 display screen
27 case data listing display window
28 case data number field
29 identification data field
30 observation image screen
31 observation image
32 time data
33 image captured positions (position within body) data
34 instruction buttons
35 replay button group
36 average color bar
37 red color detection bar
38 time bar
39 thumbnails
40 examination data search screen
41 screen topmost part
42 examination character input window
43 thumbnail display instruction button
44 report display instruction button
45 thumbnail listing screen
46 screen topmost part
47 (47-1, 47-2, . . . 47-48) thumbnails
48 scroll bar
49 scroll button
51 pop-up menu
55 report listing screen
56 screen topmost part
57 report
58 backward button
59 forward button
61 thumbnail listing display button
62 case data display button
63 search screen button Description of the Preferred Embodiments Embodiments according to the present invention are described in detail below with reference to the drawings. A basic configuration is initially described.

FIG. 1 schematically illustrates a basic configuration of a capsule endoscope system according to the present invention, and a capsule endoscope image filing system included therein.

As illustrated in FIG. 1, the capsule endoscope system 1 according to an embodiment is composed of a capsule endoscope 3 contained in a package 2, a patient who swallows the capsule endoscope 3 taken out of the package 2, namely, a person to be examined 4, a jacket 5 worn by the person to be examined 4, and a receiver 6 attachable/detachable to/from the jacket 5.

The capsule endoscope image filing system 20 is composed of a workstation 7 for executing processes such as storing, editing, etc. image data received by the receiver 6, and a recording device 9 connected to the workstation 7 via a network 8.

The recording device 9 may be an HDD (Hard Disk Drive) included in the workstation 7, an externally attached HDD, or other removable portable recording media. Alternatively, the recording device 9 maybe a server connected to the network 8.

An image capturing unit, a wireless unit, and a power supply are provided within the capsule endoscope 3. The capsule endoscope 3 wirelessly transmits image data, obtained by sequentially capturing images of digestive organs such as the esophagus, the stomach, the small intestine, the large intestine, etc. by the image capturing unit over an elapse of time, as radio waves from the wireless unit to the outside during a period spanning from when the capsule endoscope 3 is swallowed via the mouth of the person to be examined 4 in order for an observation or an examination to when it is excreted from the body.

The jacket 5 worn by the person to be examined 4 is equipped with a plurality (four in this figure) of antennas 11 (11a, 11b, 11c, 11d) that receive the radio waves of image data transmitted from the wireless unit of the capsule endoscope 3. These antennas 11 can make a wireless or wired communication with the receiver 6.

The number of the antennas 11 is not limited to four. The number may be a suitable number. Namely, the number may be any number as long as transmitted radio waves can be satisfactorily received according to the moving position of the capsule endoscope 3.

On the outer surfaces of the receiver 6, an antenna 12 used to receive image data from the jacket 5 with radio waves via the antennas 11, a display unit 13 for displaying information required for an observation or an examination, and an input unit 14 for inputting information required for the observation or the examination are provided.

At the bottom of the receiver 6, a power supply unit 15 is provided to supply power also when the receiver 6 is carried. The power supply unit 15 is implemented, for example, with a dry battery, a Li ion secondary battery, a Ni hydride battery, etc. (other types of batteries may be available as a matter of course).

Within the receiver 6, a signal processing/controlling unit 16 for executing processes required for an observation or an examination is provided, and also a slot 18 into/from which a CF (Compact Flash (registered trademark)) memory 17 for storing received image data is insertable/removable as indicated by a bidirectional arrow a illustrated in FIG. 1 is provided.

The workstation 7 is composed of a main body device 19, a monitor device 21 connected to the main body device 19, a keyboard 22, a mouse 23, etc. Additionally, the main body device 19 includes various types of interfaces in addition to an interface for making a connection to the above described network 8, although these are not illustrated.

A printer 24 and a CF memory reader/writer 25 are connected to the workstation 7 in addition to the above described receiver 6 via the interfaces.

The workstation 7 has an image processing function with which a doctor or a nurse makes a diagnosis, etc. by causing the monitor device 21 to display images within the digestive organs of the person to be examined 4, which are captured by the capsule endoscope 3.

The doctor or the nurse can issue an instruction to capture from the receiver 6 the image data of body cavities of the person to be examined 4, the image date being transmitted from the capsule endoscope 3 and received by the receiver 6, while performing an input operation with the keyboard 22 or the mouse 23 on a man-machine interface displayed on the display screen 26 of the monitor device 21 of the workstation 7.

At this time, the image data can be directly received from the receiver 6 wiredly, or can be captured from the CF memory 17 by inserting the CF memory 17 into the CF memory reader/writer 25 as indicated by an arrow b illustrated in FIG. 1.

Furthermore, the doctor or the nurse can issue instructions such as an instruction to store, in the recording device 9, image data captured from the receiver 6 as described above, an instruction to call image data stored in the recording device 9 and to make an image, associated with image data and which will be described later, be displayed on the display screen of the monitor device 21, an instruction to record diagnostic results etc. based on an observation of images to the recording device 9, and an instruction to print a medical record, etc. with the printer 24.

Figure 2:
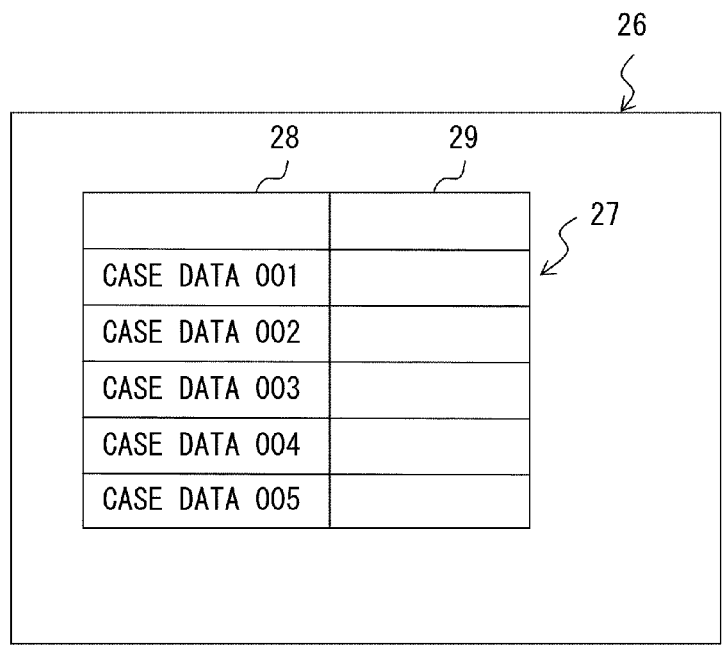
FIG. 2 illustrates an example of a listing display of case data displayed on a display screen of a monitor device of a work station in the capsule endoscope image filing system having the basic configuration illustrated in FIG. 1.

FIG. 2 illustrates an example of a listing display of examination data displayed on the display screen of the monitor device of the workstation in the capsule endoscope image filing system having the above described configuration.

On the display screen 26 of the monitor device 21 of the workstation illustrated in FIG. 1, a case data listing display window 27 is displayed as illustrated in FIG. 2 with the initial operational procedure.

In the case data listing display window 27, case data numbers are displayed in ascending order from 001 to 002, 003, . . . , in a case data number field 28 in the left portion. Additionally, identification data corresponding to each case data number in the left portion is displayed in an identification data field 29 in the right portion.

For example, at least the name and the ID of a patient, an examination date, etc. are displayed as the identification data displayed in the identification data field 29, although these are not illustrated in FIG. 2.

In FIG. 2, only five data rows are displayed in the case data number field 28 and the identification data field 29. However, all of the data rows stored in the recording device 9 can be displayed by scrolling.

If the doctor or the nurse desires to obtain the case data of a desired examination date of a desired patient while he or she is viewing identification data displayed in the identification data field 29, he or she selects the corresponding case data number, and performs an input operation—for example, double-clicks on the corresponding number with a pointing device such as the mouse, etc., so that an observation image screen is displayed.

Figure 3:
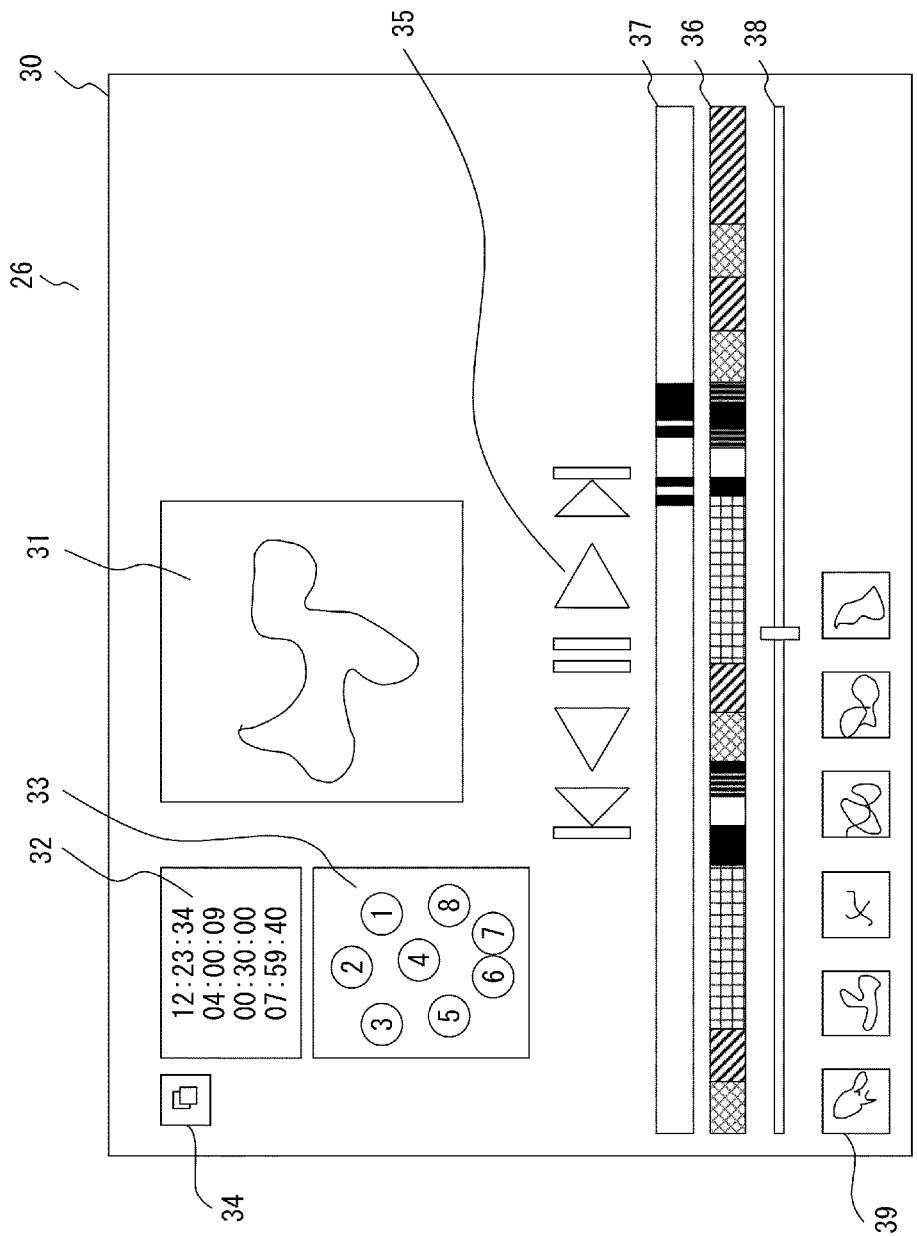
FIG. 3 illustrates an example of an observation image display screen displayed on the display screen of the monitor device of the workstation having the basic configuration illustrated in FIG. 1.

FIG. 3 illustrates an example of an observation image display screen displayed on the display screen of the monitor device of the workstation having this basic configuration. As illustrated in FIG. 3, the currently selected observation image 31 is displayed in an upper middle portion of the observation image screen 30 displayed on the display screen 26.

Four types of time data 32 associated with captured images are displayed in an upper portion at the left of the observation image 31, and image captured positions (positions within the body) data 33 is two-dimensionally displayed below the time data 32.

Additionally, a plurality (one button is illustrated as a representative in this figure) of instruction buttons 34 are displayed in an upper left portion of the display screen 26. Moreover, a replay button group 35 including replay buttons that are positioned on the right side of a stop button as a center and that are intended to respectively instruct a replay, a fast-forward replay and a frame-by-frame forward replay, and replay buttons that are positioned on the left side of the stop button and that are intended to respectively instruct a backward replay, a fast-backward replay and a frame-by-frame backward replay are displayed below the middle of the display screen 26.

Furthermore, a red color detection bar 37 and a time bar 38 are displayed above and below an average color bar 36 in a middle portion below the middle of the display screen 26.

The average color bar 36 represents average colors of captured images in positions on the time axis while the capsule endoscope 3 is moving within the organs.

A display controlling unit controls the representation of average colors to be displayed as one horizontal average color bar 36 implemented by arranging vertical lines, each of which is represented with an average color calculated for each captured image (video image) or for each of plural images along the time axis of the time bar 38, namely, in a time series in the horizontal direction of the display screen 26 in order to obtain image captured positions by using a characteristic such that colors differ depending on the organs.

In the meantime, the display controlling unit controls the display of the red color detection bar 37 so that a position (red color detected position) at which bleeding is found on the time axis is represented as a red color line within the horizontal bar on the display screen 26. The red color detection bar is one type of lesion color bar.

A lesion is not limited to bleeding. There are other lesions that can be clearly identified with images shot by the capsule endoscope 3. These lesions can be displayed with lesion color bars in blue, white or other colors other than the red color, depending on lesions.

Since bleeding is one of the most significant lesions to be focused on among lesions, the present invention is described by limiting a lesion color bar to the red color detection bar that indicates bleeding, as a representative.

Moreover, in FIG. 3, the time bar 38 is a bar that indicates the elapse of time during which the capsule endoscope 3 moves within the body of the person to be examined 4, and has a slide button.

By moving the slide button along the time bar 38 with a pointing device such as the mouse, etc., a captured image on the time axis specified with the slide button is displayed as the currently selected observation image 31.

Additionally, a series of thumbnails 39 is displayed in a horizontally scrollable manner at the bottom of the display screen 26.

Unless otherwise specified, the currently selected observation image 31 among the series of thumbnails 39 is displayed at the center, and the thumbnails 39 of the captured images consecutive to the currently selected observation image 31 in time series are displayed to the right and left sides of the currently selected observation image 31.

Alternatively, thumbnails of captured images that are sampled at predetermined time intervals or every predetermined number of thumbnails can be displayed.

(First Embodiment)

As described above, the amount of image information used for a diagnosis for each piece of case data that is obtained by conducting an examination in the past with the capsule endoscope and stored in the recording device is extremely large, and counts as many as approximately 60,000 images for each case.

If a doctor or a nurse (also referred to as a user hereinafter) desires to view his or her desired case data and a report or comments associated with the case data, he or she initially opens the display screen 26 illustrated in FIG. 2, selects a desired case data number by guessing the number while viewing case data numbers displayed in the case data listing display window 27 and considering the characteristic of the desired case data, and performs an input operation.

Then, the doctor or the nurse opens the observation image screen 30 illustrated in FIG. 3, examines the selection position of the time bar 38, observes the color tone of the average color bar 36, examines a bleeding position indicated by the red color detection bar 37, double-clicks a desired thumbnail among thumbnails 39 while viewing the horizontal listing display of the thumbnails 39 by scrolling, and enlarges and displays the thumbnail as an observation image 31.

If the observation image 31 is not an image of the case data that the doctor or the nurse is currently searching for, he or she repeatedly performs operations for changing the selection position of the time bar 38 so as to change the time point of the time series of the thumbnails 39 in the horizontal listing display, and for double-clicking the desired thumbnail.

If the desired horizontal listing display of thumbnails 39 is not expected to be obtained with the case data number that is initially selected in the case data listing display window 27 on the display screen 26 illustrated in FIG. 2, restoration is made to the case data listing display window 27 on the display screen 26 illustrated in FIG. 2 to again select a case data number.

Using the method described above, an experienced doctor or nurse requires several hours to find his or her desired case, and a doctor or nurse unfamiliar with the system or cases may require a lot of time, possibly exceeding 10 hours.

Accordingly, the present inventor devised an implementation of the workstation 7 in the capsule endoscope image filing system 20 having the above described configuration as a capsule endoscope image display device by which image information associated with the shooting of a desired position, lesional portion, etc. to be focused on can be easily grasped from among many pieces of image information (thumbnails, comments, reports, etc.). This implementation is described below as a first embodiment.

FIG. 4 illustrates an example of an examination data search screen displayed on the display screen 26 of the monitor device 21 in the capsule endoscope image display device (workstation 7) as the first embodiment.

FIG. 5 illustrates an example of a thumbnail listing screen displayed on the display screen 26 of the monitor device 21 in the capsule endoscope image display device (workstation 7) as the first embodiment.

Figure 6:
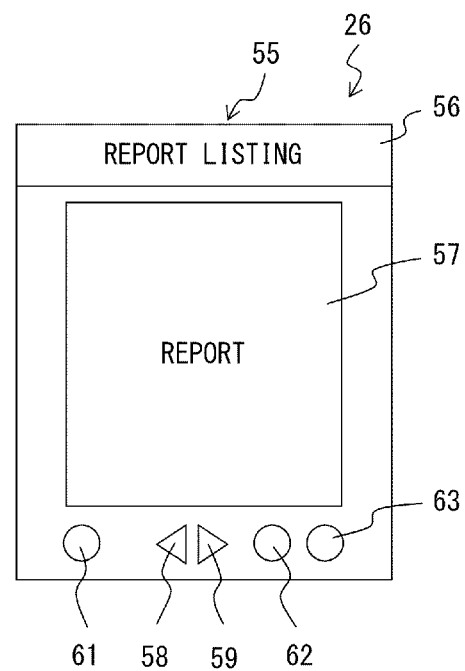
FIG. 6 illustrates an example of a report listing screen displayed on the display screen of the monitor device in the capsule endoscope image display device (workstation) as the first embodiment.

FIG. 6 illustrates an example of a report listing screen displayed on the display screen 26 of the monitor device 21 in the capsule endoscope image display device (workstation 7) as the first embodiment.

Figure 7:
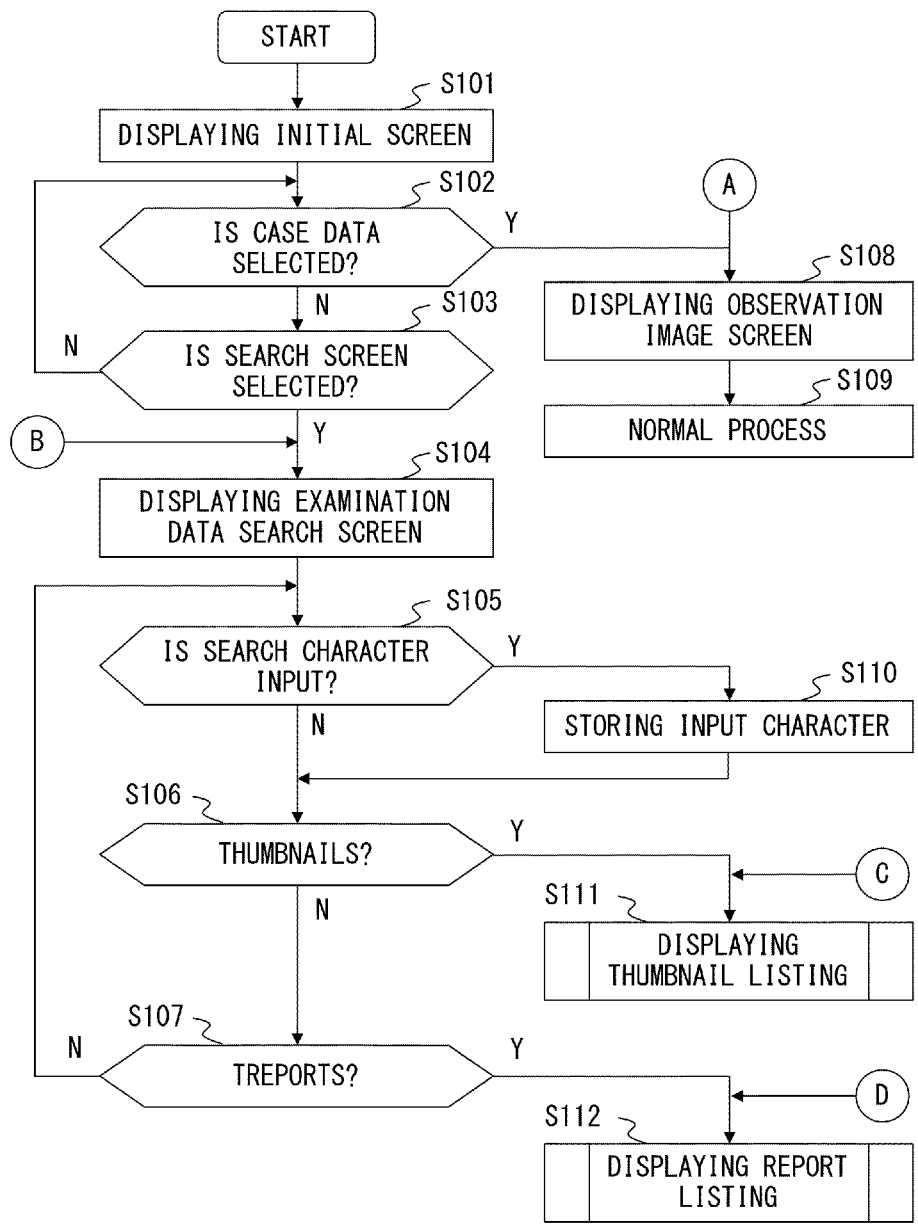
FIG. 7 is a flowchart for explaining process operations performed by a CPU, which is not illustrated, of a main body device that executes a process of a display illustrated in FIG. 4 in the first embodiment.

FIG. 7 is a flowchart for explaining process operations performed by a CPU, which is not illustrated, of the main body device 19 that executes a process of a display illustrated in FIG. 4 in the first embodiment.

Figure 8:
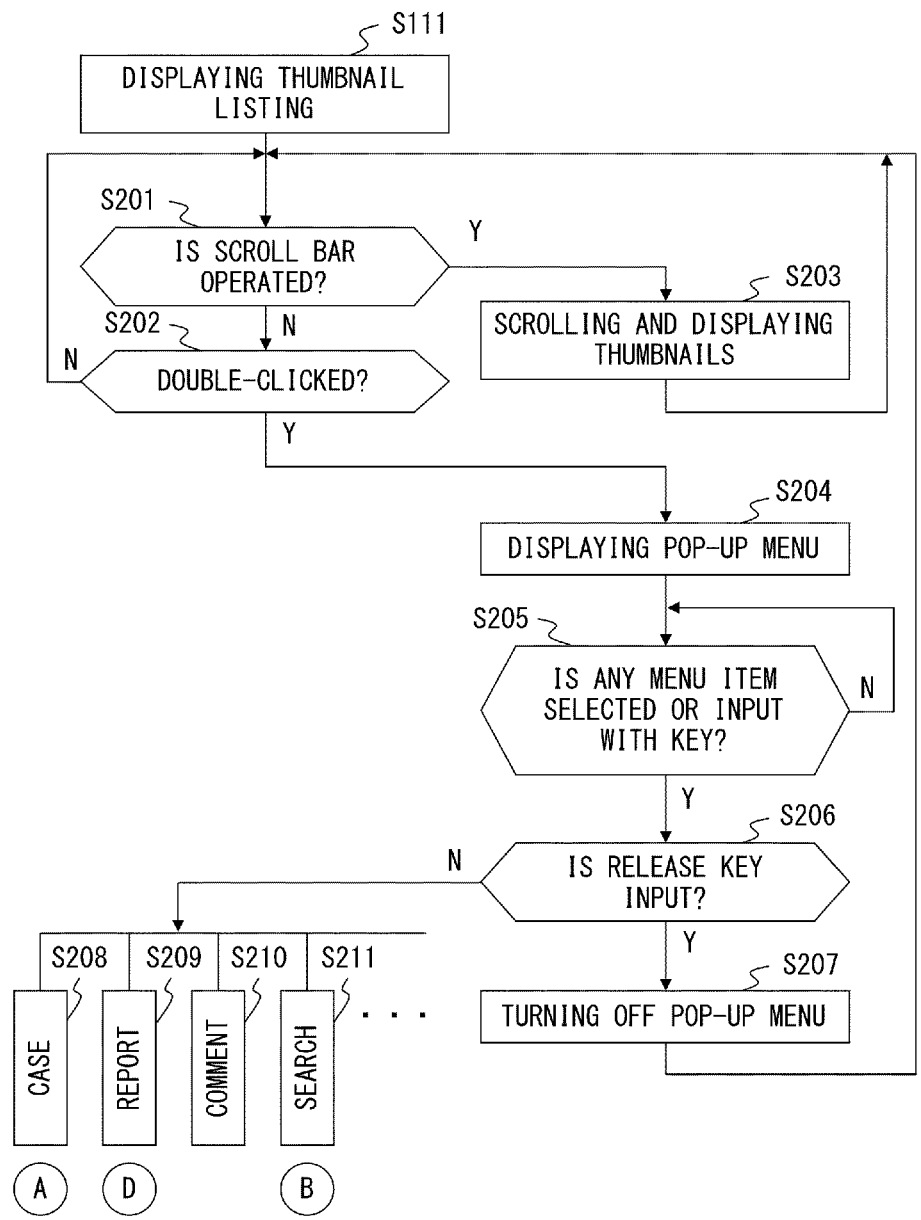
FIG. 8 is a flowchart for explaining process operations performed by the CPU, which is not illustrated, of the main body device that executes a process of a display illustrated in FIG. 5 in the first embodiment.

FIG. 8 is a flowchart for explaining process operations executed by the CPU, which is not illustrated, of the main body device 19 that executes a process of a display illustrated in FIG. 5 in the first embodiment.

Figure 9:
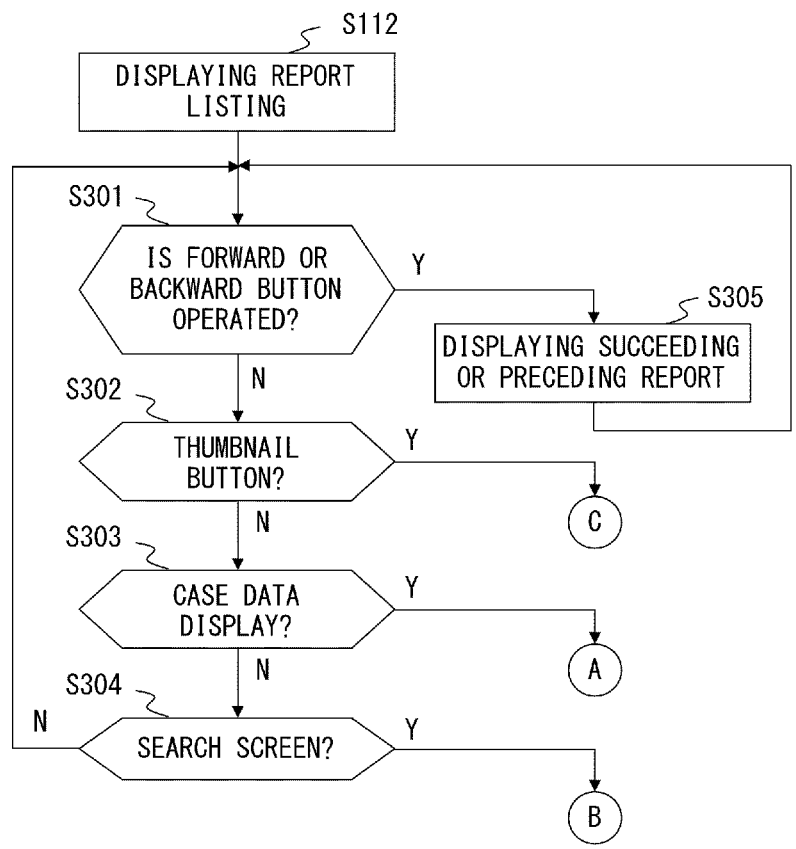
FIG. 9 is a flowchart for explaining process operations performed by the CPU, which is not illustrated, of the main body device that executes a process of a display illustrated in FIG. 6 in the first embodiment.

FIG. 9 is a flowchart for explaining process operations performed by the CPU, which is not illustrated, of the main body device 19 that executes a process of a display illustrated in FIG. 6 in the first embodiment.

Initially, once the process is started on the basis of an input operation performed by a doctor or a nurse in the flowchart illustrated in FIG. 7, the CPU displays an initial screen (Step S101).

With this process, the display screen 26 on which the case data listing display window 27 illustrated in FIG. 2 is displayed as the initial display screen is displayed. On the display screen 26 illustrated in FIG. 2, a selection button for shifting to a search screen is displayed in addition to the case data listing display window 27, although the selection button is not illustrated in FIG. 2.

The CPU determines whether or not any piece of case data is selected in the case data listing display window 27 (step S102).

If the case data is selected ("Y" in step S102), case data of the case corresponding to the case data number of the selected case data is read from the recording device, and the observation image screen 30 illustrated in FIG. 3 is displayed (step S108).

Then, the flow goes to a normal process (step S109). This normal process is the display process corresponding to an observation process executed by a doctor or a nurse, which is referred to in the basic configuration.

If the case data is not selected as a result of the determination made in step S102 ("N" in step S102), whether or not a shift to the search screen is instructed is determined next (step S103).

If the selection button for shifting to the search screen is not operated ("N" in step S103), the flow goes back to step S102. Then, the determinations in steps S102 and S103 are repeated.

If the selection button for shifting to the search screen is operated ("Y" in step S103) as a result of the determination made in step S103, a process for displaying the examination data search screen is executed (step S104). As a result, the examination data search screen 40 illustrated in FIG. 4 is displayed on the display screen 26.

On the examination data search screen 40 illustrated in FIG. 4, "examination data search display screen", the title of the screen, which indicates that this display screen is a screen for searching for examination data, is displayed in a screen top part 41.

An search character input window 42, a thumbnail display instruction button 43, and a report display instruction button 44 are displayed under the screen top part 41.

In the process illustrated in FIG. 7, the CPU initially determines whether or not search characters are input (step S105). This process is a process for determining whether or not any characters (including numerals and signs) are input in the search character input window 42 by a user on the examination data search screen 40 illustrated in FIG. 4.

If some characters are input in the search character input window 42 ("Y" in step S105), they are stored in a predetermined region of a storage device (step S110). Then, whether or not a thumbnail listing display is instructed to be displayed is determined (step S106).

Even if characters are not input in the search character input window 42 as a result of the determination made in step S105, the flow goes to the determination of step S106 next. The determination of whether or not the thumbnail listing display is instructed to be displayed is a process for determining whether or not the thumbnail display instruction button 43 is operated by the user on the examination data search screen 40 illustrated in FIG. 4.

If the thumbnail display instruction button 43 is operated ("Y" in step S106), the process for displaying the thumbnail listing screen illustrated in FIG. 5 is executed (step S111). Alternatively, if the thumbnail display instruction button 43 is not operated ("N" in step S106), whether or not a report display is instructed to be displayed is determined next (step S107).

This determination process is a process for determining whether or not the report display instruction button 44 is operated by a user on the examination data search screen 40 illustrated in FIG. 4.

If the report display instruction button 44 is operated ("Y" in step S107), a process for displaying the report listing screen illustrated in FIG. 6 is executed (step S112). Alternatively, if the report display instruction button 44 is not operated ("N" in step S107), the flow goes back to the determination process of step S105.

As described above, regardless of whether or not characters are input in the search character input window 42 by a user, the thumbnail listing screen is displayed if the thumbnail display instruction button 43 is operated, or the report listing screen is displayed if the report display instruction button 44 is operated.

The above described process for displaying the thumbnail listing screen in step S111 is described next with reference to the thumbnail listing screen illustrated in FIG. 5, and the flowchart of the thumbnail listing display process illustrated in FIG. 8.

On the thumbnail listing screen 45 displayed on the display screen 26 illustrated in FIG. 5, "thumbnail listing", the title of the screen, which indicates that this display screen is the screen for displaying a thumbnail listing, is displayed in the screen top part 46.

Additionally, forty-eight thumbnails 47 (47-1, 47-2, ..., 47-8, ..., 47-33, ..., 47-48) are displayed under the screen top part 46. Furthermore, at the end of the thumbnail listing screen 45, a scroll bar 48 and a scroll button 49 are displayed.

In the listing display of thumbnails 47, if input characters are stored in step S110, all of the thumbnails including characters that match the input characters, for example as a comment or a search key, are read from the recording device, and the first forty-eight thumbnails 47 are displayed.

Alternatively, if the input characters are not stored in step S110, all of the thumbnails stored in the recording device are read, and the first forty-eight thumbnails 47 are displayed.

In the process illustrated in FIG. 8, the CPU initially determines whether or not the scroll bar is operated (step S201). This process is a process for determining whether or not an input operation for moving the scroll button 49 upward or downward on the scroll bar 48 on the thumbnail listing screen 45 illustrated in FIG. 5 is performed.

If the input operation for moving the scroll button 49 upward or downward on the scroll bar 48 is performed ("Y" in step S201), the screen is scrolled and displayed (step S203). Then, the flow goes back to the process of step S201.

In the above described process for scrolling and displaying the screen, all of the 48 thumbnails 47 displayed on the thumbnail listing screen 45 are scrolled upward or downward and displayed according to the movement of the scroll bar 48.

Alternatively, if the input operation for moving the scroll button 49 upward or downward on the scroll bar 48 is not performed or is stopped as a result of the determination made in step S201 ("N" in step S201), whether or not the user double-clicks any of the thumbnails is determined next (step S202).

If the user does not double-click any of the thumbnails ("N" in step S202), the flow goes back to the process of step S201. Then, the determinations made in steps S201 and S202 are repeated. In contrast, if the user double-clicks any of the thumbnails ("Y" in step S202), a pop-up menu is displayed from the double-clicked thumbnail (step S204).

The example of the thumbnail listing screen 45 illustrated in FIG. 5 is an example where the thumbnail 47-33 is double-clicked, and the pop-up menu 51 is displayed from the thumbnail 47-33.

In the pop-up menu 51, menu items for shifting the screen, such as a case display, a report display, a comment display, a search screen display, etc. are displayed.

Here, the CPU determines whether or not the user selects any of the menu items in the pop-up menu 51 (step S205), or waits until any of the menu items is selected ("N" in step S205).

If the user selects any of the menu items in the menu ("Y" in step S205), whether or not the selected menu item is a release key is determined (step S206). If the selected menu item is the release key ("Y" in step S206), the display of the pop-up menu is turned off (step S207). Then, the flow goes back to the process of step S201.

Alternatively, if the selected menu item is not the release key ("N" in step S206), a display process corresponding to the selected menu item is executed.

Namely, if the user clicks to select, for example, the case display as the selection operation, the flow goes to the process of step S108 illustrated in FIG. 7 in order to display the observation image screen 30 that is associated with the thumbnail 47-33 and illustrated in FIG. 3 (step S208).

In this process, an enlarged image of the thumbnail 47-33 is displayed as the observation image 31 in the upper middle portion of the observation image screen 30. Moreover, if the user clicks to select the report display in the pop-up menu 51, the flow goes to a report listing display process in step S112 of FIG. 7 in order to display the report listing that is associated with the thumbnail 47-33 and illustrated in FIG. 6 (step S209).

Alternatively, if the user clicks to select the comment display in the pop-up menu 51, a comment (normally, a comment on the thumbnail 47 is stored in the recording device by being linked to the corresponding thumbnail) that is not illustrated and associated with the thumbnail 47-33 is displayed (step S210).

Still alternatively, if the user clicks to select the search screen display in the pop-up menu 51, the flow goes to the process of step S104 illustrated in FIG. 7 in order to display the examination data search screen illustrated in FIG. 4 regardless of which of the thumbnails 47 the pop-up menu 51 is displayed from (step S211).

As described above, in the thumbnail listing display, only thumbnails associated with a desired case are selectively listed and displayed. If a thumbnail to be focused on is included in the thumbnails, a case, a report, or a comment associated with the thumbnail can be immediately viewed.

Next, the report listing screen display process in step S112 of FIG. 7 is described with reference to the report listing screen illustrated in FIG. 6 and the flowchart of the report listing display process illustrated in FIG. 9.

On the report listing screen 55 displayed on the display screen 26 illustrated in FIG. 6, "report listing", the title of the screen, which indicates that this display screen is a screen for displaying a report listing, is displayed in a screen top part 56.

Additionally, a report 57 is displayed at the center of the report listing screen 55, and a backward button 58 and a forward button 59 are displayed in a middle portion under the report 57. Moreover, a thumbnail listing display button 61 is displayed to the left of these buttons, whereas a case data display button 62 and a search screen button 63 are arranged side by side to the right of the buttons 58 and 59.

In the listing display of the report 57, if the input characters are stored in step S110, all of the reports including characters that match the input characters are read from the recording device, and the first report 57 is displayed.

Alternatively, if the input characters are not stored in step S110, all of reports 57 stored in the recording device are read, and the first report 57 is displayed.

Here, the CPU determines whether or not the forward or backward button (the backward button 58 or the forward button 59) is operated in FIG. 9 (step S301).

If the forward or backward button is operated ("Y" in step S301) and if the operated button is the forward button 59, the report 57 read immediately after the currently displayed report 57 is displayed. If the operated button is the backward button 58, the report 57 read immediately before the currently displayed report 57 is displayed (step S305). Then, the flow goes back to the process of step S301.

If the forward or backward button is not operated as a result of the determination made in step S301 ("N" in step S301), whether or not the thumbnail button (thumbnail listing display button 61) is operated is determined next (step S302).

If the thumbnail button is operated ("Y" in step S302), the flow goes to the process of step S111 illustrated in FIG. 7 in order to execute the process for displaying the thumbnail listing screen illustrated in FIG. 5.

Alternatively, if the thumbnail button is not operated as a result of the determination made in step S302 of FIG. 9 ("N" in step S302), whether or not the case data display button 62 is operated is determined next (step S303).

If the case data display button 62 is operated ("Y" in step S303), the flow goes to the process of step S108 illustrated in FIG. 7 in order to display the observation image screen 30 for observing case data, which is illustrated in FIG. 3.

Alternatively, if the case data display button is not operated as a result of the determination made in step S303 of FIG. 9 ("N" in step S303), whether or not the search screen button 63 is operated is determined next (step S304).

If the search screen button 63 is operated ("Y" in step S304), the flow goes to the process of step S104 illustrated in FIG. 7 in order to display the examination data search screen 40 illustrated in FIG. 4.

Alternatively, if the search screen button 63 is not operated as a result of the determination made in step S304 of FIG. 9 ("N" in step S304), the flow goes back to step S301. Then, the process of step S301, S302, S303 or S304 is repeated.

As described above, the normal observation procedures require bothersome operations such that the observation image screen illustrated in FIG. 3 is opened from the case data listing display illustrated in FIG. 2, and a guessed thumbnail 39 is clicked on to be displayed as the observation image 31 and observed while referencing the average color bar 36, the red color detection bar 37, the time bar 38, etc., and the procedures starting at FIG. 2 must be repeated if the thumbnail 39 is different from a desired one.

According to the present invention, however, thumbnails including search characters as a comment or a search key, or reports including the search characters are listed and displayed on the basis of an input of the search characters as in the above described first embodiment, whereby data associated with an image obtained by shooting a desired position, lesional portion, etc. to be focused on, can be easily grasped from among many pieces of image information.

As a result, when, for example, a doctor creates materials to be presented in an academic conference, he or she can easily find necessary data, which offers convenience to the doctor.

The present invention is not limited to the above described embodiments, and can be practically modified in a variety of ways within a scope that does not depart from the gist of the present invention.

What is claimed is:

1. A capsule endoscope image display device for storing, in a recording device, image information of a plurality of images obtained by being captured in a plurality of positions within a body to be examined over an elapse of time by an image capturing device introduced into the body to be examined, for reading the image information from the recording device, and for displaying the read image information on a display screen, comprising:

image displaying means for displaying a capsule endoscope image;
   thumbnail generating means for generating a thumbnail of an image to be focused on from the capsule endoscope image;
   thumbnail storing means for recording the generated thumbnail in the recording device;
   report creating means for creating a report of a capsule endoscope examination;
   report storing means for storing the created report in the recording device;
   search screen displaying means for displaying a search character input window on the display screen;
   search character inputting means for inputting a character in the search character input window;
   thumbnail searching means for searching for a thumbnail to which a comment including a same character as the character input in the search character input window has been added, or which includes supplementary information including the same character;
   thumbnail listing display means for displaying a listing of thumbnails searched for by the thumbnail searching means on the display screen;
   report searching means for searching for a report including the same character as the character input in the search character input window, or which includes supplementary information including the same character; and
   report listing displaying means for displaying a listing of reports searched for by the report searching means on the display screen.

2. The capsule endoscope image display device according to claim 1, wherein
   the search screen displaying means can specify a search target together with the search character input window.

3. The capsule endoscope image display device according to claim 2, wherein
   the search target that the search screen displaying means can specify is a thumbnail.

4. The capsule endoscope image display device according to claim 3, wherein
   if there is no character input in the search character input window and if a thumbnail specification input button is operated, the thumbnail searching means sequentially reads all thumbnails stored in the recording device, and causes the thumbnail listing displaying means to display a listing of the thumbnails in a scrollable manner.

5. The capsule endoscope image display device according to claim 4, further comprising
   thumbnail observation screen displaying means for enlarging and displaying any of the thumbnails by default in an observation screen region on a case data display screen if the case data display associated with the any of the thumbnails in the listing display is specified.

6. The capsule endoscope image display device according to claim 2, wherein
   the search target that the search screen displaying means can specify is a report.

7. The capsule endoscope image display device according to claim 6, wherein
   if there is no character input in the search character input window and if a report specification input button is operated, the search screen displaying means sequentially reads all reports stored in the recording device, and causes the report listing displaying means to display a listing of the reports in a scrollable manner.

8. The capsule endoscope image display device according to claim 1, wherein
   the thumbnail listing displaying means displays a listing of thumbnails in a scrollable manner on the display screen.

9. The capsule endoscope image display device according to claim 8, wherein
   the thumbnail listing displaying means displays specifying means that can specify at least a case data display, a report screen display, a search screen display, and/or a comment screen display, associated with a specified thumbnail, when any of the thumbnails in the listing display is specified.

10. The capsule endoscope image display device according to claim 9, wherein
    the thumbnail listing displaying means displays an observation screen for observing case data in accordance with a pressing of a case display menu provided in the specifying means.

11. The capsule endoscope image display device according to claim 9, wherein
    the thumbnail listing displaying means displays a listing of reports in accordance with a pressing of a report display menu provided in the specifying means.

12. The capsule endoscope image display device according to claim 9, wherein
    the thumbnail listing displaying means displays a comment associated with a thumbnail in accordance with a press of a comment display menu provided in the specifying means.

13. The capsule endoscope image display device according to claim 9, wherein
    the thumbnail listing displaying means displays an examination data search screen in accordance with a pressing of a search screen display provided in the specifying means.

14. The capsule endoscope image display device according to claim 9, further comprising
    thumbnail observation screen displaying means for enlarging and displaying any of the thumbnails by default in an observation screen region on a case data display screen if the case data display associated with the any of the thumbnails in the listing display is specified.

15. The capsule endoscope image display device according to claim 1, wherein
    the report listing displaying means displays a listing of reports in a scrollable manner on the display screen.

16. The capsule endoscope image display device according to claim 1, wherein
    the report displaying means displays a listing of thumbnails in accordance with a press of a thumbnail button provided on the display screen.

17. The capsule endoscope image display device according to claim 1, wherein
the report displaying means displays an observation screen for observing case data in accordance with a press of a case data display button provided on the display screen.

18. The capsule endoscope image display device according to claim 1, wherein
the report displaying means displays an examination data search screen in accordance with a pressing of a search screen button provided on the display screen.

19. The capsule endoscope image display device according to claim 1, wherein
the report listing displaying means displays specification buttons for specifying at least a thumbnail listing display, and a case data display associated with a report currently being displayed, along with the listing display of reports.

20. The capsule endoscope image display device according to claim 1, wherein
the recording device includes an internal HDD (hard disk drive), an externally attached HDD, a recording medium, or a network server.

21. A capsule endoscope image display program for storing, in a recording device, image information of a plurality of images obtained by being captured in a plurality of positions within a body to be examined over an elapse of time by an image capturing device introduced into the body to be examined, for reading the image information from the recording device, and for displaying the read image information on a display screen, comprising:

an image displaying step of displaying a capsule endoscope image;
a thumbnail generating step of generating a thumbnail of an image to be focused on from the capsule endoscope image;
a thumbnail storing step of recording the generated thumbnail in the recording device;
a report creating step of creating a report of a capsule endoscope examination;
a report storing step of storing the created report in the recording device;
a search screen displaying step of displaying a search character input window on the display screen;
a search character inputting step of inputting a character in the search character input window;
a thumbnail searching step of searching for a thumbnail to which a comment including a same character as the character input in the search character input window is added, or which includes supplementary information including the same character;
a thumbnail listing displaying step of displaying a listing of thumbnails searched for by the thumbnail searching step on the display screen;
a report searching step of searching for a report including the same character as the character input in the search character input window, or which includes supplementary information including the same character; and
a report listing displaying step of displaying a listing of reports searched for by the report searching step on the display screen.

* * * * *